US006472365B1

(12) United States Patent
Titball et al.

(10) Patent No.: US 6,472,365 B1
(45) Date of Patent: Oct. 29, 2002

(54) PHARMACEUTICALS AND ASSAYS USING ENZYME SUBUNITS

(75) Inventors: Richard W Titball, Salisbury (GB); Francis J Carr, Aberdeen (GB)

(73) Assignee: Biovation Limited, Aberdeen (GB)

( * ) Notice: Subject to any disclaimer, the term of this patent is extended or adjusted under 35 U.S.C. 154(b) by 0 days.

(21) Appl. No.: 08/894,527

(22) PCT Filed: Feb. 21, 1996

(86) PCT No.: PCT/GB96/00380

§ 371 (c)(1), (2), (4) Date: Mar. 16, 1998

(87) PCT Pub. No.: WO96/25952

PCT Pub. Date: Aug. 29, 1996

(30) Foreign Application Priority Data

Feb. 22, 1995 (GB) ................................................ 9503486

(51) Int. Cl.[7] ........................ A01N 61/00; A01N 37/18; A61K 39/395
(52) U.S. Cl. ........................... 514/1; 514/2; 424/130.1; 424/134.1; 424/141.1; 424/152.1
(58) Field of Search ........................... 514/1, 2, 44, 12; 424/130.1, 141.1

(56) References Cited

U.S. PATENT DOCUMENTS

| | | | | |
|---|---|---|---|---|
| 4,874,710 A | * | 10/1989 | Piran | ........................... 436/518 |
| 4,900,556 A | | 2/1990 | Wheatley et al. | |
| 5,277,913 A | * | 1/1994 | Thompson et al. | ........... 424/450 |
| 5,356,633 A | * | 10/1994 | Woodle et al. | ............... 424/450 |
| 5,653,996 A | * | 8/1997 | Hsu | ............................ 424/450 |

FOREIGN PATENT DOCUMENTS

| | | |
|---|---|---|
| EP | A 0 301 333 | 2/1989 |
| JP | 5-56797 | 9/1993 |
| WO | WO 87/03205 | 6/1987 |

OTHER PUBLICATIONS

Flickinger et al., Cytotoxiciy of Antibody–Phospholipase C Conjugates on Cultured Friend Leukemia Cells, Sep. 1975, Europ.J. Cancer, vol. 12, pp. 159–160.*
Titball et al., FEMS Microbiology Letters, vol. 110, pp. 45–50, 1993.*
Kim et al., J. Immunological Methods, vol. 170, pp. 225–231, 1994.*
Titball et al., Infection and Immunity, vol. 59 (5), pp. 1872–1874, May 1991.*
Heidenreich et al., Molecular Medicine Today, vol. 1, No. 3, pp. 128–133, 1995.*
Verma et al., Nature, vol. 389, pp. 239–242, Sep. 1997.*
Eck et al., Goodman & Gilman's The Pharmacological Basis of Therapeutics, McGraw–Hill, New York, pp. 77–101, 1996.*

Fugman et al Biochimica et Biophysica Acta. 795 (1984) 191–195 Lipoprotein Lipase– and Phospholipase $A_2$–Catalyzed Hydrolysis of Phospholipid Vesicles with an Encapsulated Fluorescent Dye.

Titball et al Infection and Immunity vol. 59 No. 5 5/91 pp. 1872–1874Hemolytic and Sphingomyelinase Activities of *Clostridium perfringens* Alpha–Toxin are Dependent on a Domain Homologous to that of an Enzyme etc.

Titball et al FEMS Microbiology Letters 110 (1993) 45–50 Biochemical and immunological properties of the C–terminal domain of the alpha–toxin of *Clostridium perfringens*.

McFarland et al Biochimica et Biophysica Acta 876 (1986) 438–449 1,2–Dipalmitoyl–3–β–2–Furylacryloyltriacylglycerol: a chromophoric substrate for lipoprotein lipase.

Kim et al J. of Immunological Methods 170 (1994) 225–231 Liposome immunoassay (LIA) for gentamicin using phospholipase C.

Buxton et al Microchemical Journal 34, 349–354 (1986) Quantitation of Phospholipase C Activity Using Alklaine Phosphatase impregnated Liposomes.

Wu et al Analytical Biochemistry 221, 152–159 (1994) A Continuous Fluorometric Assay for Phospholipases Using Polymerized Mixed Liposomes.

Immunology (1972), 23(5), 705–11 Coden:Immuam, 1972, XP002006372 Hesketh, T. R. et al: "Complement and phospholipase C lysis of lipid membranes" see the whole document.

Database Chemabs Chemical Abstracts Service, Columbus, Ohio, US AN–117:187810, Kotani, Kyoshi: "Rupture–release of contents from liposomes with phospholipase" XP002006373 see abstract & JP,A,04 200 632 (Toyo Ink Mfg. Co, Ltd.

Bioconjugate Chemistry, vol. 4, No. 3, May 1, 1993, pp. 199–205, XP000367865 Babbitt B: "Contact–Dependent, Immunecomplex–Mediated Lysis of Hapten–Sensitized Liposomes" see p. 204, col. 1, paragraph 3.

* cited by examiner

*Primary Examiner*—Deborah J. R. Clark
*Assistant Examiner*—Shin-Lin Chen
(74) *Attorney, Agent, or Firm*—Nixon & Vanderhye P.C.

(57) ABSTRACT

A method of releasing an agent for example, a chemotherapeutic, under predetermined conditions by protecting the agent within a lipid structure such as a liposome, causing lipase activity to be constituted by combining two or more components, e.g., recombinant N- or C-terminal *Clostridium perfringens* alpha-toxin fragments, one of these components being conjugated to a targeting molecule e.g., an antibody which binds to a target such as a tumor antigen. The lipid structure is then exposed to the constituted lipase activity such as to release the agent. Also disclose are materials and kits for use in the method.

10 Claims, 5 Drawing Sheets

1 = 100pM α-TOXIN
2 = N-T
3 = C-T
4 = N+C t-TEST PERFORMED AT 5% LEVEL:
C vs N+C  t = -2.95
         p = 0.026  :- SIGNIFICANTLY DIFFERENT

N vs N+C  t = -4.15
         p = 0.006  :- SIGNIFICANTLY DIFFERENT

ANTIBODY CONJUGATED N-TERMINAL
α-TOXIN FRAGMENT

ANTIGEN PRESENTING TARGET CELL
(CANCER CELL)

B)

ANTIBODY BINDING

C)

ADMINISTER C-TERMINAL α-TOXIN
FRAGMENT

RESTORATION OF ENZYME ACTIVITY
AT THE TARGET CELL SURFACE

D)

ADMINISTER LIPOSOME CONTAINING
ANTI-CANCER AGENT

E)

α-TOXIN MEDIATED LIPOSOMAL LYSIS
(LIPO-BURST) RESULTS IN LOCALISED
RELEASE OF ANTI-CANCER AGENT

ANTIBODY CONJUGATED
α-TOXIN

ANTIGEN PRESENTING TARGET CELL
(CANCER CELL)

B)

ANTIBODY BINDING

C)

ADMINISTER LIPOSOME CONTAINING
ANTI-CANCER AGENT

D)

α-TOXIN MEDIATED LIPOSOMAL LYSIS
(LIPO-BURST) RESULTS IN LOCALISED
RELEASE OF ANTI-CANCER AGENT

Fig.4.

A) ABSENCE OF ANALYTE

⊙ LIPOSOME+ REPORTER MOLECULES

B) PRESENCE OF ANALYTE

"LIPO-BURST"

N̄ = ANALYTE-CONJUGATED N-TERMINAL α-TOXIN FRAGMENT

C = C-TERMINAL α-TOXIN FRAGMENT

▼ = FREE ANALYTE

Y = ANTI-ANALYTE ANTIBODY

PHARMACEUTICALS AND ASSAYS USING ENZYME SUBUNITS

This application is a 33 U.S.C. 371 of PCT/GB96/00380 filed Feb. 21, 1996, and claims benefit to GB 95 03486.4, filed Feb. 22, 1995.

The present invention relates to methods for releasing an agent under pre-determined conditions, for example at a pre-determined site or in the presence of a pre-determined material, and in particular for releasing an agent for therapeutic, diagnostic or investigative purposes. The invention further relates to pharmaceutical compositions incorporating such methods, materials and kits for use in such methods. It is frequently desirable in the bioscience field to be able to deposit or release a particular agent under, pre-determined conditions, for instance at a specific site within an organism or to mark the presence or absence of an analyte during an assay. At present such specificity is frequently achieved by use of antibodies bound directly to active agents. For instance tumour associated monoclonal antibodies (MABS) have been used to selectively carry chemotherapeutic drugs to tumour cells. Clinical studies have investigated the delivery of methotrexate in patients colorectal carcinoma (Ballantyne et al. 1988. Int. J. Cancer, 42: 103–108) and also the use of adriamycin (see "Principles of Cancer Biotherapy" Ed. Oldham, R. K., Pub. Raven Press, New York, 1987). Similarly. MABS conjugated to toxins such as ricin, abrin, Pseudomonas toxin, Diptheria toxin and other have also been used as anti-cancer agents. Studies in vitro and in vivo have indicated that such conjugates can be extremely toxic to tumour cells ( Roffler et al. 1991. Cancer Res. 51:4001–4007; Embleton et al 1991; Bri. J. Cancer 63:670–674).

The use of MABS to provide selectivity avoids the side-effect problems associated with traditional chemotherapeutic treatment of cancer either in metastatic disease or in an adjuvant or primary setting. However, a major problem arises because many agents require internalisation before killing the target cell. Additionally immunotoxins usually give rise to unacceptable toxicity due to interaction with non-target cells during passage to the site.

A potential alternative delivery system for selected agents is based around the use of synthetic liposomes. Liposomes were originally described in 1974 (Bangham e al. Methods Membr. Biol. 1: 1–68). Liposomes consist of one or more phospholipid bilayers arranged in concentric rings of alternate aqueous spaces. Many compounds (both lipid and Water soluble) including cancer chemotherapeutics, antimicrobial drugs, enzymes, hormones and nucleic acids have been incorporated into either the aqueous or lipid phase of liposomes. The behaviour of drug-containing liposomes in animal and human subjects has formed the subject of several studies (Gregoriadis 1990, Immunol. Today 11: 89–97).

Thus liposomes offer considerable promise as vehicles for delivery of agents for use in a variety of applications including biochemical and immunological assays, diagnosis, and also pharmaceutical delivery systems for eternal and parenteral use. Unfortunately their application is undermined by the difficulty associated with selectively releasing their contents at a specific time or location.

The present invention has now provided methods for releasing a selected agent at a specific disease site or at a specific time or location and pharmaceutical compositions incorporating such methods, kits and materials for use in such methods, which seek to address some, and in preferred forms all, of the aforementioned problems.

According to a first aspect of the present invention there is provided a method of releasing an agent under predetermined conditions comprising the steps of protecting the agent within a lipid structure, causing lipase activity to be constituted in response to the predetermined conditions, and exposing the lipid structure to the constituted lipase activity such as to release the agent.

By lipase is meant any enzyme which hydrolyses lipids and includes, but is not limited to. enzymes which hydrolyse complex lipids such as phospholipids and grycolipids.

The term constituted as used herein is intended to denote localised, created or significantly increased i.e. a significant achievement or increase in lipase activity is initiated when the predetermined conditions are met.

A large number of naturally occurring lipases are known. For instance many gram-positive and negative bacteria produce enzymes having phospholipase C (PLC) activity. These enzymes hydrolyse phospholipids with varying efficiencies and posses a variety of haemolytic and lethal properties which generally makes them unsuitable for administration to living subjects.

One characterised enzyme is *Clostridium perfringens* alpha-toxin (CPAT). CPAT promotes direct lysis of certain mammalian cells and is the most toxic PLC described to date (see McDonel, J.L. (1986) pp 617–655 "Pharmacology of Bacterial Toxins" Eds. Dorner & Drews, Pub. Pergamon Press, Oxford). CPAT is a peptide containing 370 amino acids.

Preferably the lipid structure employed by the present invention comprises a phospholipid membrane defining a core. More preferably the lipid structure is a liposome. The agent to be released is chosen in accordance with the precise application in which the invention is being employed, however the nature of the agent must be such that it is protectable by a lipid structure.

Preferably the lipase activity employed in the present invention comprises a PLC activity, and more preferably is derived from CPAT. CPAT activity has not previously been demonstrated against liposomes; however the inventors of the present invention have shown that CPAT has significant activity against liposomes.

Preferabiy the lipase activity employed in the present invention is constituted by combining two or more components whereby the lipase activity of the product formed by the components is greater than the sum of the individual components, or alternatively the lipase activity is constituted at a specific location normally with much less or no lipase activity by virtue of the localisation of the lipase either as a holoenzyme or a combination of two or more components in either case in combination with a targeting molecule.

More preferably the components correspond to, or are derived from, an active lipase holoenzyme such that their recombination recovers all or part of the activity of the holoenzyme lipase preferably at a specific location. These components may both be proteins—however the invention embraces all systems wherein lipase activity is enhanced. localised or recovered by the combination of two or more components, including non-protein components such as co-factors.

Most preferably the components are derived from or include CPAT.

The N-terminal two-thirds of CPAT shares sequence homology with the phosphatidylcholine-PLC from *Bacillus cereus*. It has been demonstrated that N-terminal recombinant truncated CPAT (aa 1–249) retains phosphatidylcholine hydrolysing activity but has reduced sphingomyelinase activity and is neither haemolytic nor lethal. (Titball et al 1991. Infect. Immun. 59:1872–1874). Recombinant protein comprising the C-terminal third of CPAT (aa 247–370) is devoid of sphingomyelinase and haemolytic activity and is not toxic for murine lymphocytes (Titball et al. 1993, FEMS Microbiology Letters 110: 4550). It has been demonstrated that haemolytic activity (as assessed by an in vitro murine erythrocyte lysis assay) can be restored when the N-terminal and C-terminal recombinant proteins are added together (reconstituted CPAT).

The inventors of the present invention have shown that reconstituted CPAT has significant activity against liposomes.

The pre-determined conditions of the present invention may require that the agent be released only in the vicinity of a tumour or pathogen, or in the presence of an anaiyte or DNA sequence, or under any other suitable detectable condition.

Preferably the achievement of predetermined conditions is causally related to the constitution of lipase activity at a specific location by conjugating at least one of the lipase components or the holoenzyme to a targeting molecule capable of specific binding to a predetermined target under the pre-determined conditions. Suitable targeting molecules include antibodies, antigens, receptors, ligands and nucleic acid probes or primers.

Thus the achievement of conditions may be conveniently related (via a specific antigen-antibody binding event, or the annealing of a nucleotide probe to a specific sequence, or to some other specific physical process) to the constitution of lipase activity in the presence of a predetermined target. Thereafter the addition of suitable lipid structures e.g. liposomes, to the system will effectively lead to target-induced liposomal lysis.

Thus in one embodiment of the invention, which may be used to release an agent at a predetermined target site, the targeting molecule is an antibody which has been raised such as to bind to an antigen on a target site. The antibody is conjugated to a first lipase component such that the component binds at the site. A second lipase component is also added to the system and binds at the site. A second lipase component is also added to the system and binds to the first such that lipase activity is constituted at the site without having had fully active lipase circulating in the system. Liposome containing a suitable agent may be added to the system such that they are lysed on contacting the constituted lipase thereby releasing the agent locally at the site.

It should be noted that the second lipase component may be added independently of in association with, or as an integral part of the liposomes. In another embodiment of the invention which may be used to release an agent at a predetermined target site, the targeting molecule is an antibody which has been raised such as to bind to an antigen on a target site. The antibody is conjugated to a lipase holoenzyme such that the holoenzyme binds at the site. Liposomes containing a suitable agent may be added to the system such that they are lysed on contacting the constituted lipase thereby releasing the agent locally at the site.

Thus these embodiments have in vivo applications for the treatment or locating of a disease through the targeted delivery of membrane-lytic enzyme activity. Unbound antibody-component conjugate may be cleared from the system prior to adding the second component so as to ensure only local constitution of lipase activity. Specific ablation of the diseased cells or organism may then be achieved by addition of liposomes containing disease modulating compounds. Use of the present invention against tumours may therefore provide an improved killing index due to the ability to release a high local concentration of compound at the tumour and also possible beneficial by-stander effects wherein non-antigen bearing cancer cells in the immediate locality of the tumour will also be the subject of chemotherapeutic killing.

Suitable compounds may include reporter molecules, cytotoxic drugs, lymphokines. anti-inflammatories, anti-fungals, anti-malarials and other drugs combating infectious diseases. synthetic oligonucleotides, nucleic acids (e.g. plasmids) etc, additional antibodies active as immunotoxins, enzymes for conversion of inactive to active pharmaceutical compounds etc. The precise compounds to be used will occur to those skilled in the art according to the problem to be solved.

In a second embodiment of the invention, which may be used for detecting the presence of an antigen in a system, the targeting molecule is an antigen conjugated to a first lipase component. The antigen-1st component conjugate is mixed with antibody raised against authentic antigen such that the antibody binds to the conjugated antigen. The presence of the bound antibody sterically prevents the constitution of lipase activity in the presence of a second lipase component. When the antibody/antigen-component complex is in the presence of authentic antigen the antibody is sequestered by and binds to the authentic antigen. This means that lipase activity will be constituted in the presence of the second lipase component. This event (and hence the presence of authentic antigen) can be detected by addition of liposomes containing a suitable marker e.g. dye, to the system.

Thus this embodiment has in vitro application as an homogenous assay system for the detection of biological or other analytes. The antigen may be conjugated to one of the lipase constituents by recombinant or biochemical techniques.

In another embodiment of the invention, which may be used for detecting the presence of an antigen in a system, the targeting molecule is an antibody conjugated either to a first lipase component or a holoenzyme. The antibody-lipase conjugate may be attached to a specific antigen which has become associated with a solid phase either by direct binding to the solid phase or by binding via an antibody or other intermediate molecule. The presence of antigen can be measured following attachment of the conjugate and washing-off or elution of the excess conjugate by the addition of liposomes containing a suitable marker eg dye.

As an alternative for the detection of an antigen in a system, the antigen could also be attached to a solid phase either directly by absorption or chemical linkage or indirectly via another antibody or binding agent which is, in turn, attached to a solid phase. The antibody-lipase conjugate comprising either the complete lipase or one component is then added followed by if required, the second lipase component and followed by suitable compound-containing liposomes.

In a third embodiment, which may be used for detecting the presence or location of a specific nucleotide sequence in a system, a suitable complementary probe is attached to one or both lipase components such that annealing of the probe or probes to the sequence causes lipase activity to be constituted at that site. This event (and hence the presence of the sequence) can be detected by addition of liposomes containing a suitable marker e.g. dye to the system.

As an alternative for the detection of a specific nucleotide sequence in a system the nucleotide sequence could also be attached to a solid phase either directly by absorption or chemical linkage or indirectly via a complementary nucleotide sequence or an antibody or binding agent which is, in turn, attached to a solid phase. The probe-lipase conjugate comprising either the complete lipase or one component is then added followed by if required, the second lipase component and followed by suitable compound-containing liposomes.

Also embraced by the present invention are materials for use in the methods above.

Thus in a second aspect of the invention there is provided a first lipase component capable of combining with a second lipase component such that the lipase activity of the product formed by the components is greater than the sum of the individual components, said first lipase component being conjugated to targeting molecule capable of specific binding to a predetermined target.

Also embraced by the present invention are pharmaceutical preparations comprising a targeting molecule conjugated with a lipase holoenzyme or lipase component and liposomes containing pharmaceutically active compounds or compounds capable of conversion into pharmaceutically active molecules.

Also embraced by the present invention are kits for use in the methods above.

Thus in a third aspect of the invention there is provided a kit for use in the methods above comprising a first lipase component capable of combining with a second lipase component such that the lipase activity of the product formed by the components is greater than the sum of the individual components, said first lipase component being conjugated to targeting molecule capable of specific binding to a predetermined target, and further comprising the second lipase component.

Preferably the kit still further comprises liposomes containing a suitable agent for use in the methods above.

Preferably the lipase components are CPAT holoenzyme or N-terminal recombinant CPAT and C-terminal recombinant CPAT as herein before described.

A range of alternative lipases may be applicable for use in the current invention. These alternatives include lipases from bovine and porcine pancreas, bee venom, Crotalus venom and include phospholipase B from *S.violaceoruber* and phospholipase C from Vibrio sp. and *B. cereus*. It will also be understood that, as an alternative to non-human lipases in pharmaceutical preparations from the current invention, lipases of human origin might be substituted or alternatively non-human lipases such as CPAT might be genetically engineered or modified in order to escape recognition by the human immune system.

Where two or more lipase components are used in the method of the present invention or for substances and materials thereof, it might be possible to improve the strength of association of these lipase components in order to more quickly or more fully reconstitute enzyme activity. This might be achieved by, for example, genetic engineering or by use of auxiliary components which themselves associate thus bringing the lipase components together.

Thus CPAT or reconstituted CPAT activity may be used to direct the lysis of synthetic liposomes containing biologically active preparations or detectable molecule such as dyes thereby providing inter alia a mechanism for targeted drug delivery in vivo, or a reporter system for homogenous and discontinuous assay systems in vitro.

A range of alternative liposomes may be applicable for use in the current invention—the invention embraces all types of liposome.

The methods of the present invention will now be described, by way of illustration only, through reference to the following examples and figures. Other embodiments falling within the scope of the invention will occur to those skilled in the art in the light of these.

Figures

EXAMPLES

Example 1

Liposome Lysis By Recombinant CPAT Holoenzyme

The ability of purified recombinant CPAT (holoenzyme) to induce liposome lysis was tested using liposomes containing carboxyfluoroscein substrate, lysis being assessed using a fluoremetric assay. Carboxyfluoroscein release was measured for 60 minutes using CPAT concentrations between 1 pM and 1 $\mu$M.

Figure 1:
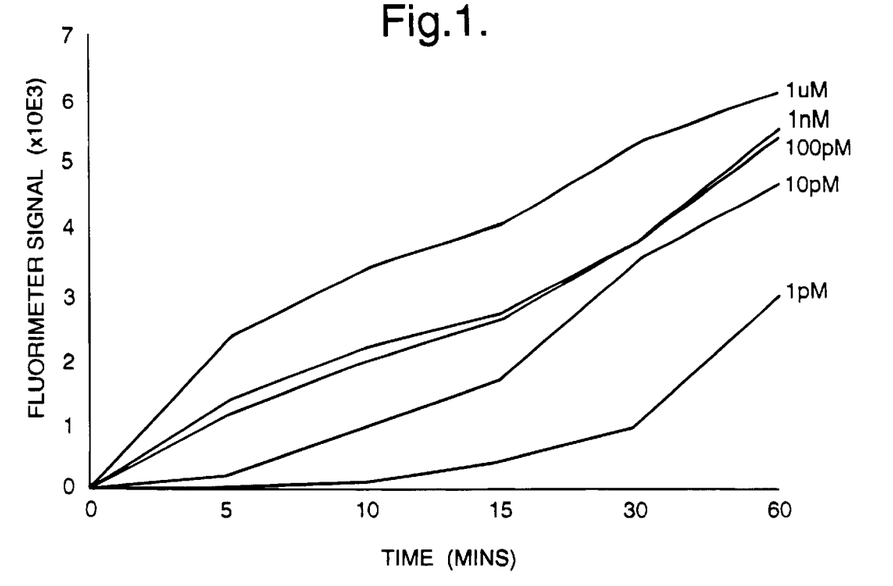
FIG. 1 Demonstrates the ability of purified recombinant CPAT (holoenzyme) to induce liposome lysis in an experiment carried out as described in Example 1.

The results shown in FIG. 1, clearly show that CPAT can induce liposome lysis.

Sphingomyelin liposomes containing 5-(6)-carboxyfluorescein were prepared using the method described by Senior and Gregoriadis (1983) in liposome technology (Gregoriadis ed.) vol. 111 pp263–82, CRC Press, Boca Raton, Fla. A thin film of a mixture of sphingomyelin and $\beta$-oleoyl-$\gamma$-cholesterol (1:1 w/w, 35.5 mg total) in chloroform was dried under nitrogen and carboxyfluorescein (20 mM) added. The mixture was placed in a bath sonicator at 40° C. and then left at 22° C. for 1 hour before sonication (10×1 min with 0.5 min between cycles, 40° C.; Heatsystems XL-200 sonicator with 19 mm probe) to generate small unilamellar vesicles. The free carboxyfluorescein was separated from the liposomes using gel filtration chromatography (Sephadex G-25; Pharmacia PD10 column) with borate buffered saline (BBS; 0.2 M sodium metaborate, 7.5 g/l NaCl, 1.8 g/i $CaCl_2.2H_2O$, pH adjusted to 7.5 with boric acid) as the eluting buffer. Fractions containing liposomes were collected and stored at 4° C.

Liposomes were diluted in BBS and 25 $\mu$l of enzyme added to 2.5 ml volumes of the diluted liposomes. The mixture was incubated at 37° C. and fluorescence measured using a Perkin-Elmer L5-5B spectrofluorimeter with exitation at 485 nm (10 nm slit width) and emission measured at 520 nm (5 nm slit width).

The additon of C. perfringens $\alpha$-toxin (ph myelin produced a time-dependent increase in 6-carboxyfluorescein fluorescence. The rate of increase in fluorescence was related to the concentration of enzyme over the range tested (10 pM to 10 nm final concentration see FIG. 1). In the absence of $Ca^{2+}$ there was a four-fold decrease in the activity of the a-toxin (100 pM) against sphingomyelin liposomes.

The effect of $Cpa_{1-249}$ (N-domain) and $Cpa_{247-370}$ (C-domain) on carboxyfluorescein release was that the individual domains of the α-toxin ($Cpa_{1-249}$ and $Cpa_{247-370}$) were incubated individually and together with liposomes containing 6-carboxyfluorescein. The results indicate that neither $Cpa_{1-249}$ nor $Cpa_{247-370}$ alone were able to induce 6-carboxyfluorescein fluorescence from sphingomyelin liposomes. However, when both $Cpa_{1-249}$ and $Cpa_{247-370}$ were incubated with sphingomyelin liposomes an increase in fluorescence was detected.

Example 2

Comparative Activity of CPAT Holoenzyme and N- and C-Fragments

The comparative activity against liposomes of purified recombinant CPAT (holoenzyme). separate recombinant N- and C-CPAT, and mixed recombinant N-and C-CPAT was measured using a fluoremetric assay. In each case the concentration was 100 pM of each protein.

Figure 2:
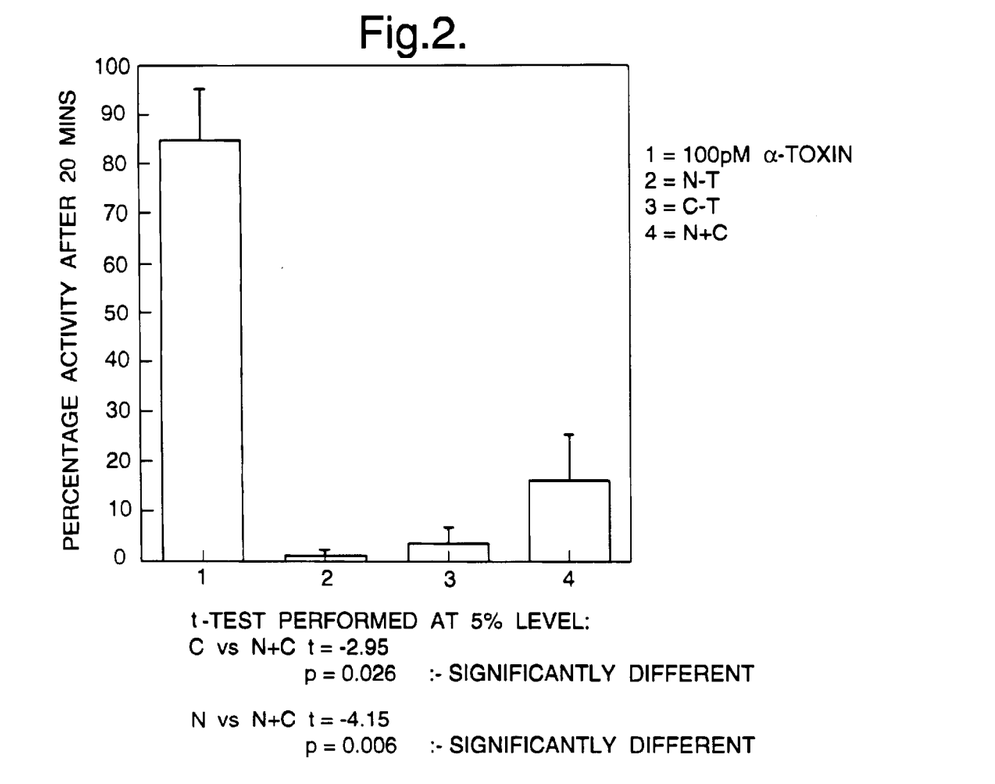
FIG. 2 Demonstrates the comparative activity against liposomes of i) purified recombinant CPAT (holoenzyme); ii) recombinant N-CPAT; iii) recombinant C-CPAT and iv) mixed recombinant N- and C-CPAT. The experiment was carried out as described in Example 2.

The results, shown in FIG. 2, clearly show enhanced liposome degradation by combined N- and C-CPAT compared to the sum of their separate activities.

Example 3

Method of Delivering Chemotherapeutics in Vivo

Figure 3:
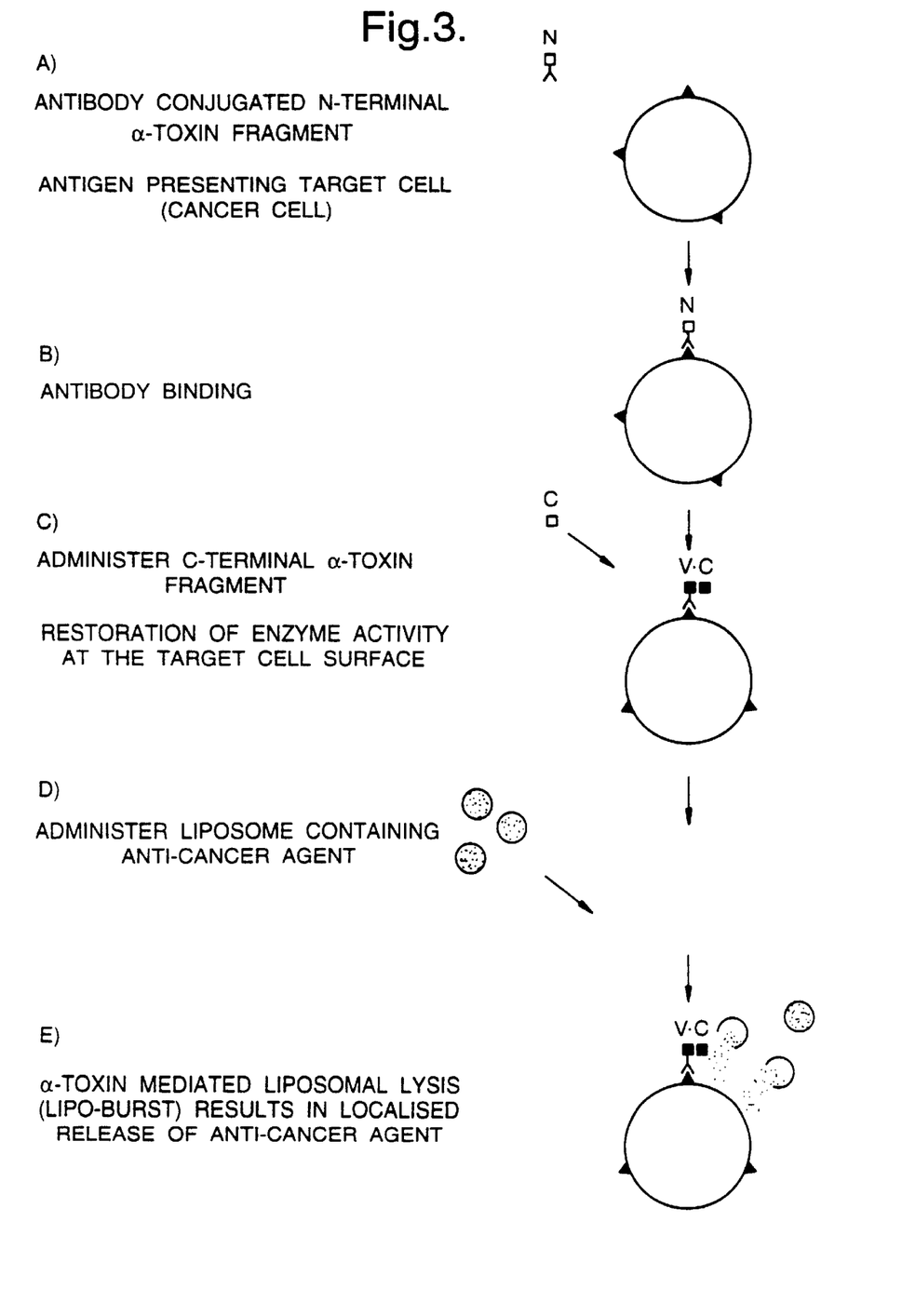
FIG. 3 Shows a schematic diagram illustrating the in vivo anti-cancer method described in Example 3.
Figure 3B:
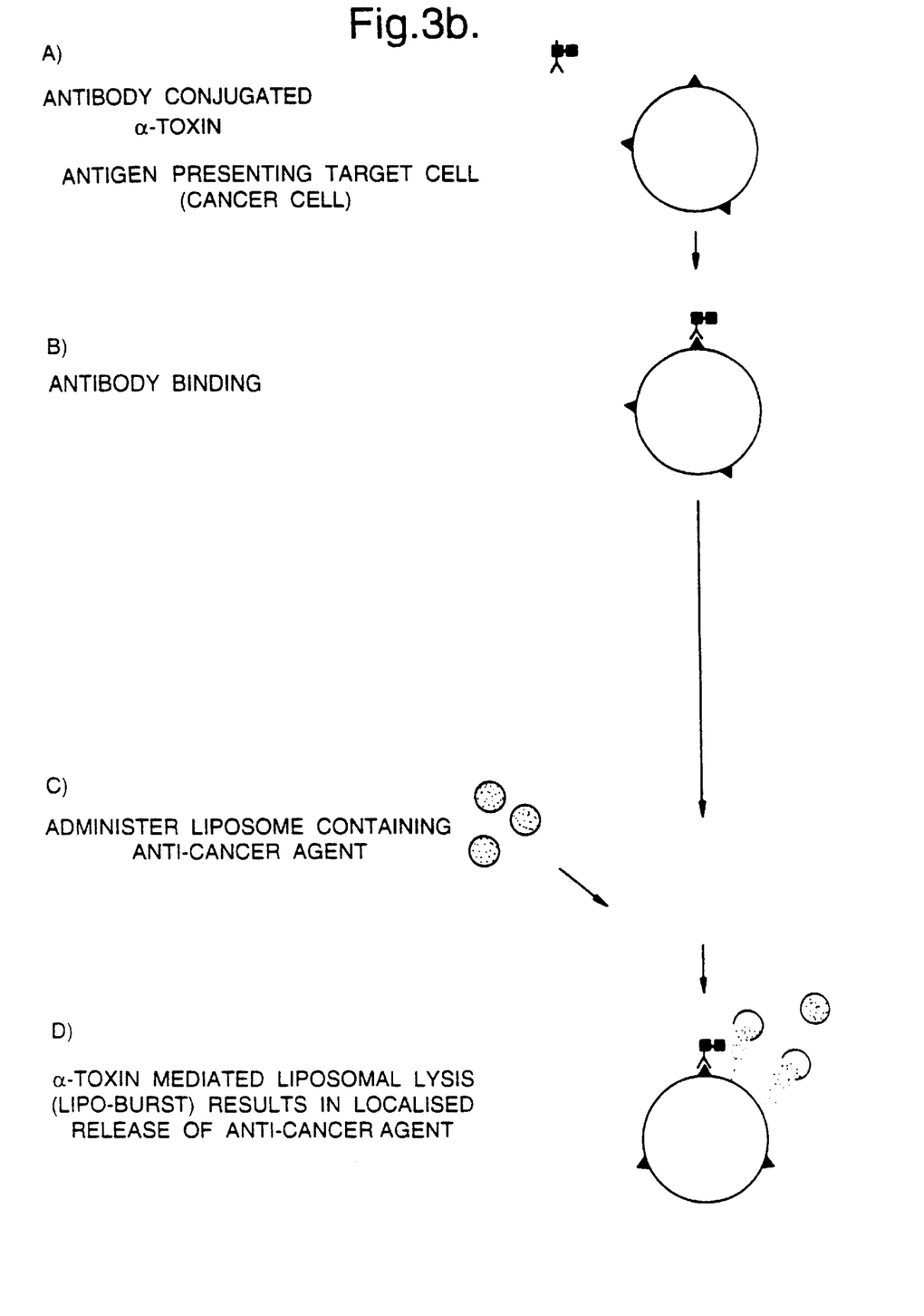
FIG. 3b Shows a schematic diagram illustrating the in vivo anti-cancer method similar to that described in Example 3 wherein the holoenzyme is conjugated to the antibody.

An in vivo anti cancer method was provided as shown in FIG. 3. In this method the invention is used to target chemotherapeutics at cancer cells. C-CPAT (the smaller CPAT fragment) is conjugated to an antibody specific to a tumour (A) and is administrated in vivo. The conjugated antibody binds at the tumour site (B) and the complementary (N-CPAT) fragment is administrated thereby causing lipase activity to be constituted at the target cell surface (C). Liposomes containing a chemotherapeutic (adriamycin) are administered (D) either contemporaneously with or subsequent to the N-CPAT. The restored CPAT activity at the tumour mediates liposomal lysis thereby achieving high local concentrations of chemotherapeutic agent (E).

In an alternative method the liposomes are used to deliver anti-inflammatory drugs or biological response modifiers to antigen presenting cells or damaged tissues containing reactive infiltrating disease lymphocytes.

It will be appreciated that the general methodology of Example 3 has wide application in the field of therapeutic medicine.

Example 4

Method of Genetically Modifying Cells in Vivo

An in vivo method for modifying the genetic nature of cells was provided as follows. The method is similar to that described in Example 3 except that the liposomes are used to deliver anti-proliferative synthetic oligonucleotides to proliferating cells (such as endothelial cells).

It will be appreciated that the methodology of Example 4 may be used in the treatment of many genetically based disorders e.g. cardiorestinosis, and will be of value in numerous therapeutic or experimental strategies which are dependent on the delivery of new genetic information to cells in diverse disease settings.

Example 5

An Homogeneous in Vitro Analyte Detection Assay

Figure 4:
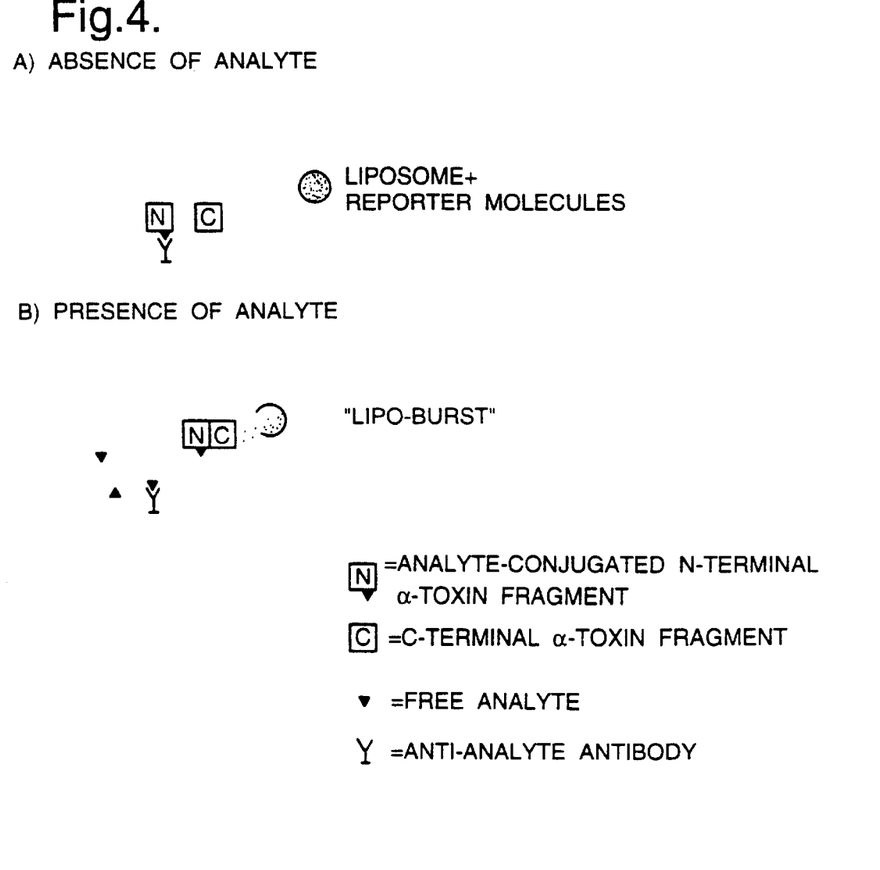
FIG. 4 Shows a schematic diagram illustrating the in vitro antibody-mediated antigen detection assay described in Example 5.

An antibody-mediated in vitro analyte detection assay was provided as shown in FIG. 4.

First an analyte is conjugated to N-CPAT and the analyte/N-CPAT conjugate is mixed with an antibody raised against the analyte which binds thereto. This complex is mixed with C-CPAT and liposomes containing a reporter molecule in a system suspected of containing analyte. In the absence of analyte the constitution of CPAT activity is sterically prevented by the antibody and the liposomes remain intact (A). In the presence of analyte the antibody is sequestered from the N-CPAT complex thus allowing CPAT activity to be constituted and liposomal lysis to occur thereby releasing the reporter molecules (B).

It will be appreciated that such a detection system will have wide application in diagnostic and research fields.

Example 6

An in Vitro Nucleic Acid Hybridisation Assay

Figure 5:
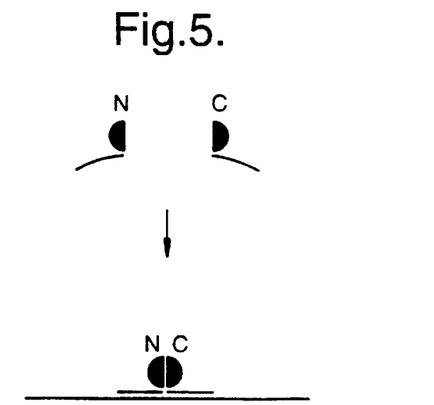
FIG. 5 Shows a schematic diagram illustrating the in vitro nucleic acid hybridisation assay described in Example 6.
Figure 6:
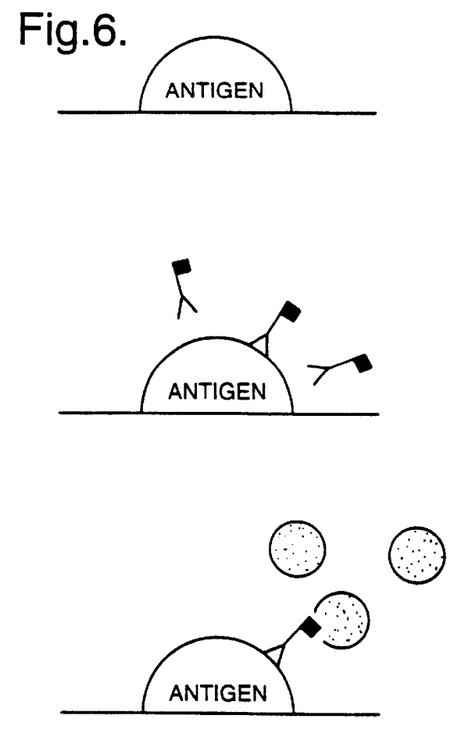
FIG. 6 Shows binding of antibody-lipase to an antigen on a solid phase and subsequent liposomal lysis.

An in vitro nucleic acid sequence detection assay was provided as employing conjugated probes as shown in FIG. 5.

Nucleic acid molecules (probes) capable of hybridising to the sequence to be detected such that they are adjacent each other are conjugated to N-CPAT and C-CPAT. The conjugates are added to a system suspected of containing the sequence. In the presence of the sequence hybridisation of the probes occurs thereby bringing the N-CPAT and C-CPAT into proximity and restoring CPAT activity. The restoration is signalled by liposomal lysis and the release of detectable molecules such as dyes.

It will be appreciated that such a detection system may be applied in both an homogenous assay (no solid phase or separation step) and discontinuous assay (where the target sequence is bound to a solid phase format).

Figure 7:
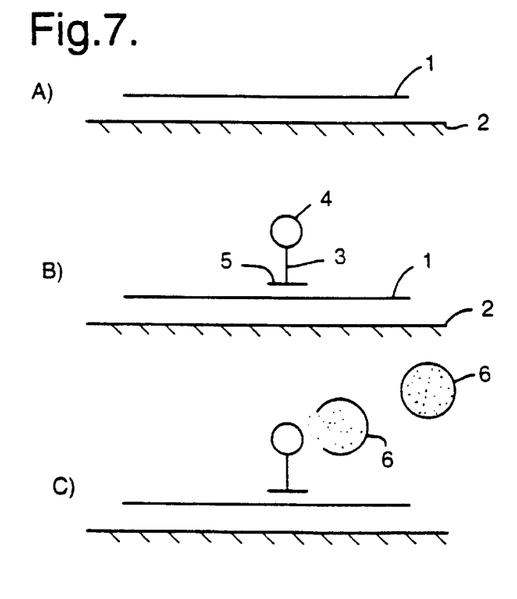
FIG. 7 Shows binding of antibody-lipase to a nucleotide sequence on a solid phase and subsequent liposomal lysis.

FIG. 7 illustrates an in vitro nucleic acid detection assay. A nucleotide sequence 1 is attached to a solid phase 2 either directly or indirectly. The probe lipase component 3 comprising the lipase 4, which may be the complete lipase or one component, is then added followed by if required, the second lipase component. The probe lipase component 3 also comprises a short nucleotide sequence 5 which is complementary to part of the nucleotide sequence 1. Liposomes 6 are added to the system and are lysed on contact with the probe lipase component 3, thus releasing the contents of the liposomes.

The lipase comprising C.perfringens alpha toxin N-terminal domain corresponds to that which possesses phospholipase activity—typically this may include residues from 1–260 which in turn may include some or all of the amino acids in this range and the C-terminal domain which confers liposome lysing properties, typically may include residues from 240 to 370 which in turn may include some or all of the amino acids in this range.

The following experimental methods illustrate the killing of cancer cells using liposome-conjugated antibodies in conjunction with liposome-encapsulated drugs.

Anti-CEA antibodies are targetted with conjugated Clostridium perfringens phospholipase C holoenzyme to HeLa cells in vitro. Following binding of antibody lipase conjugate to the cells, excess conjugate is removed and drug liposomes are added. The antibody-conjugate phospholipase C breaks open the liposomes, releasing the cytotoxic drug, leading to an enhanced killing of the cancer cells. Appropriate controls are included to identify background cell death due to non-specific endocytosis of drug-liposomes or any possible lipase activity acting directly on the cancer cell.

Conjugation of Phospholipase C to Anti-CEA Antibody

Anti-CEA antibody was obtained from the Scottish Antibody Production Unit (Carluke, Scotland). Recombinant Clostridium perfringens phospholipase C was produced as described in the literature. The anti-CEA antibody was conjugated to the phospholipase C using Sulfo-MBS (Pierce and Warriner, Chester, England) according to the manufacturer's instructions. Unconjugated antibody or phospholipase C was removed by dialysis.

Enhanced Killing of HeLa Cells Using Anti-CEA-Phospholipase C Conjugate in Conjunction with Drug Liposomes 100 ml of HeLa cells in DMEM+10% foetal calf serum were plated into each well of a 96 well tissue culture plate and cells were allowed to grow to semi-confluency. The growth media was removed and replaced with 100 ml of various concentration of antibody-enzyme conjugate diluted in DMEM +10% FCS. The conjugate was allowed to bind with the cells for 3 hours at 37° C. After this incubation the unbound Antibody-enzyme conjugate was removed by washing 3× with DEME +10% FCS. After washing, 100 ml of various concentrations of DaunoXomes (Nexstar Pharmaceutical Ltd, Cambridge, England) diluted in DMEM +10% FCS was added to the wells and incubation allowed to continue at 37° C. for 16–24 hours. An estimate of the number of viable cells was obtained using a 'Celltiter 96 cell proliferation assay' (Promega, Southampton, England).

At 1:100 dilution of liposomes, viable cells were reduced by <50% without phospholipase C or conjugated antibody. The addition of approximately 10 μg/ml conjugate resulted in a reduction of viable cell count >50% whilst the addition of phospholipase C had no effect on the liposome induced reduction in viable cells. If liposomes were added directly with phospholipase C or conjugated antibody to cells, then no reduction in viable cell count was obtained indicating destruction of the liposomes in solution.

What is claim is:

1. A method for releasing at least one pharmaceutical agent at a site of a target comprising the steps:

A binding an antibody to said target wherein said antibody is conjugated

I) to a lipase wherein the lipase is able to lyse liposome, or     II) to at least a first lipase component having no or less lipase activity in comparison to a corresponding lipase holoenzyme, and B) I) wherein when said antibody is conjugated to a lipase able to lyse liposomes, contacting a liposome containing said pharmaceutical agent with said antibody conjugated to a lipase such that the liposome can be lysed by the lipase, or     II) wherein when said antibody is conjugated to the at least a first lipase component,       a) adding a second lipase component which reconstitutes the lipase activity of said at least a first lipase component at least partially by binding to the first lipase component and, subsequently, contacting a liposome containing said pharmaceutical agent with the reconstituted lipase such that the liposome can be lysed by the reconstituted lipase activity, or       b) adding a liposome containing said pharmaceutical agent to said antibody conjugated to the at least a first lipase component wherein the liposome is associated with a second lipase component able to reconstitute the lipase activity of the at least a first lipase component by binding to the first lipase component wherein said second lipase component is an integral part of the liposome.

2. A method as claimed in claim 1 wherein unbound antibody which is conjugated to the first lipase component is cleared prior to adding the second lipase component or the liposomes associated with the second lipase component.

3. A method as claimed in claim 1 wherein the target site is a tumor, a diseased cell or a pathogenic organism.

4. A method as claimed in claim 1 wherein the pharmaceutical agent is selected from the group consisting of a reporter molecule, a chemotherapeutic cytotoxic drug, a lymphokine, an anti-inflammatory, an anti-fungal agent, or an anti-malarial agent.

5. A method of delivering a chemotherapeutic comprising a method as claimed in claim 1 wherein the agent is a chemotherapeutic cytotoxic drug.

6. A method as claimed in claim 5 for killing of neoplastic cells and/or inhibiting growth of neoplastic cells.

7. A method of delivering an anti-inflammatory drug comprising a method as claimed in claim 1 wherein the agent is an anti-inflammatory drug.

8. A method as claimed in claim 1 wherein the lipase activity comprises phospholipase C activity.

9. A method as claimed in claim 8 wherein the phospholipase C activity comprises CPAT.

10. A method as claimed in claim 1 wherein the lipase components are N-terminal recombinant CPAT and C-terminal recombinant CPAT.

* * * * *